United States Patent [19]

Kurokawa et al.

[11] Patent Number: 5,291,404
[45] Date of Patent: Mar. 1, 1994

[54] RADIOTHERAPY TREATMENT PLANNING SYSTEM

[75] Inventors: Masaaki Kurokawa; Masataka Nagao, both of Hyogo, Japan

[73] Assignee: Mitsubishi Denki Kabushiki Kaisha, Tokyo, Japan

[21] Appl. No.: 680,421

[22] Filed: Apr. 4, 1991

[30] Foreign Application Priority Data

Apr. 18, 1990 [JP] Japan .................................. 2-102117
Aug. 9, 1990 [JP] Japan .................................. 2-209242

[51] Int. Cl.⁵ .............................................. G06F 15/42
[52] U.S. Cl. ........................... 364/413.26; 364/413.25; 364/413.27; 250/263
[58] Field of Search ...................... 364/413.26, 413.25, 364/413.27; 250/263.1

[56] References Cited

U.S. PATENT DOCUMENTS 4,992,663 2/1991 Takeo .............................. 250/327.23

OTHER PUBLICATIONS

J. A. Purdy, "Computer Applications in Radiation Treatment Planning", Radiation Medicine, vol. 1, No. 2, 1983, pp. 161-173.

T. R. Mackie et al., "A Convolution Method of Calculating Dose for 15-MV X Rays", Med. Phys. 12(2), Mar./Apr. 1985, pp. 188-196.

*Primary Examiner*—Roy N. Envall, Jr.
*Assistant Examiner*—Gita Shingala
*Attorney, Agent, or Firm*—Rothwell, Figg, Ernst & Kurz

[57] ABSTRACT

The radiotherapy treatment planning system is for calculating the radiation dose to be absorbed by an object to be irradiated, prior to radiotherapy. The distribution of contribution output unit outputs the distribution of contribution showing the contribution rates of scattered beam or electron beam to an observational point in each point of the object to be irradiated. The arithmetic unit calculates the absorbed dose of the observational point due to the scattered beam or the absorbed dose due to the electron beam, by summing up each contribution rate multiplied with the electron density at the point corresponding thereto.

18 Claims, 9 Drawing Sheets

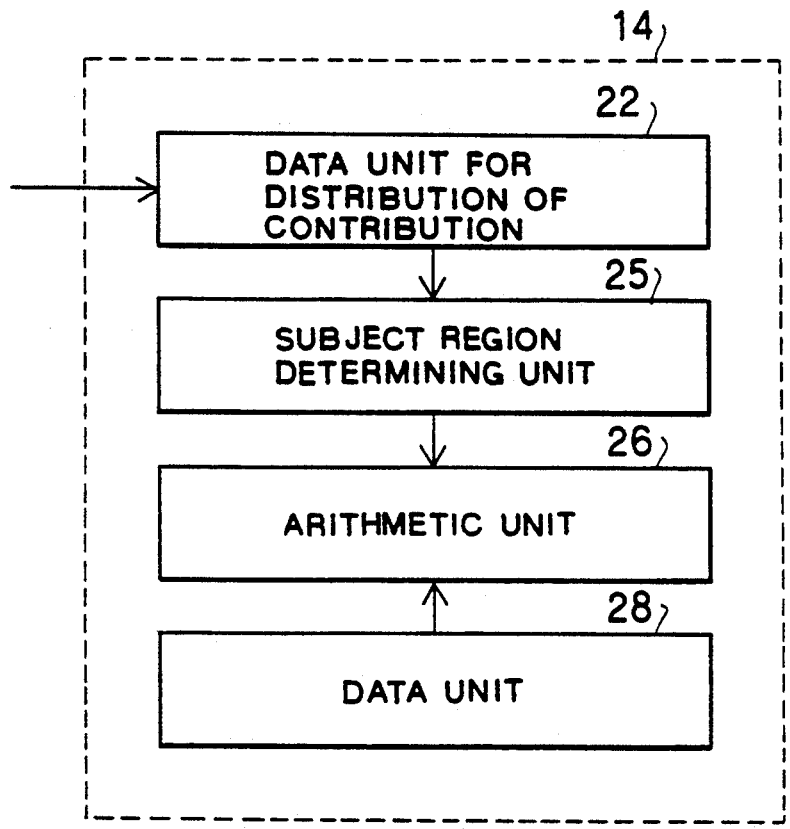
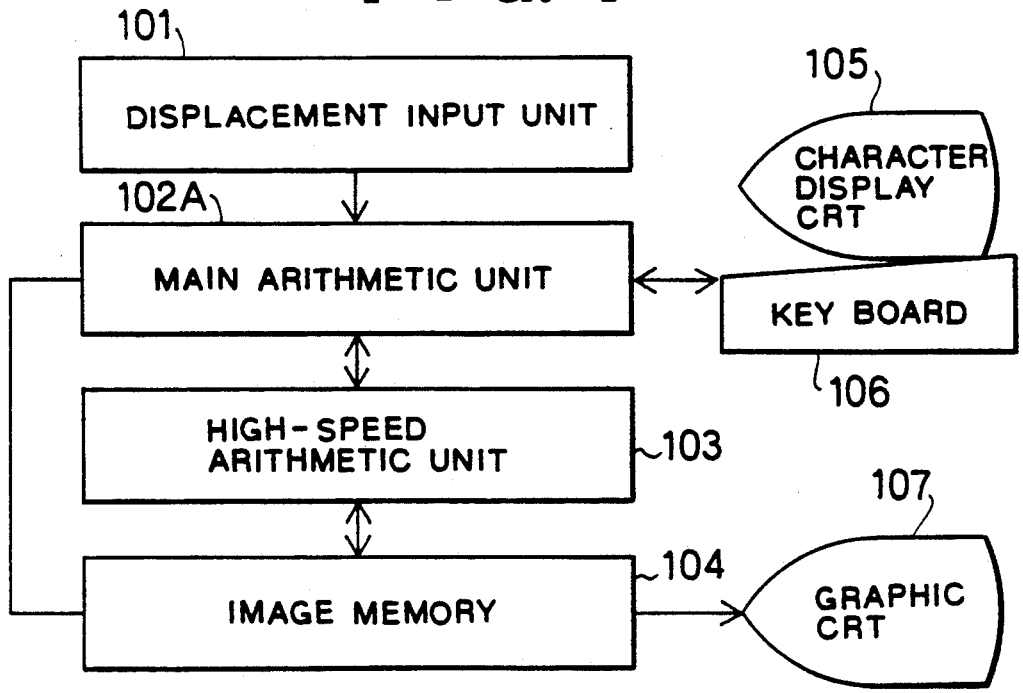

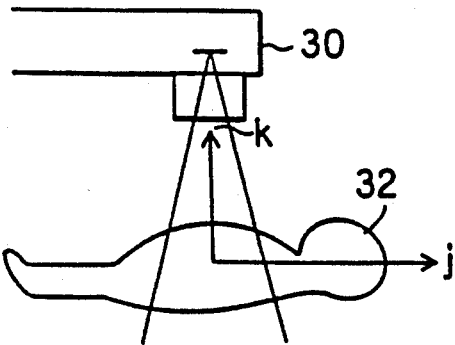
F I G. 18 (A)
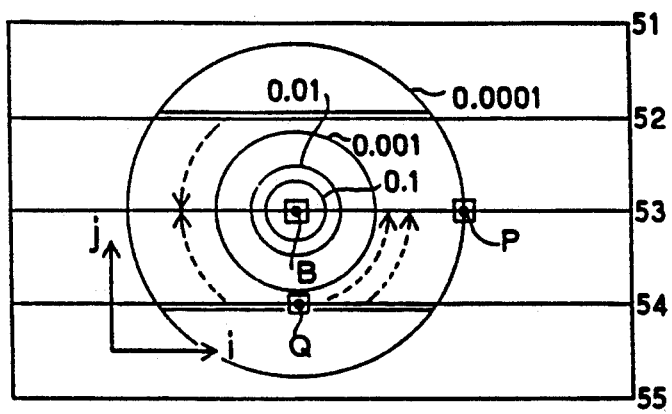
F I G. 18 (B)
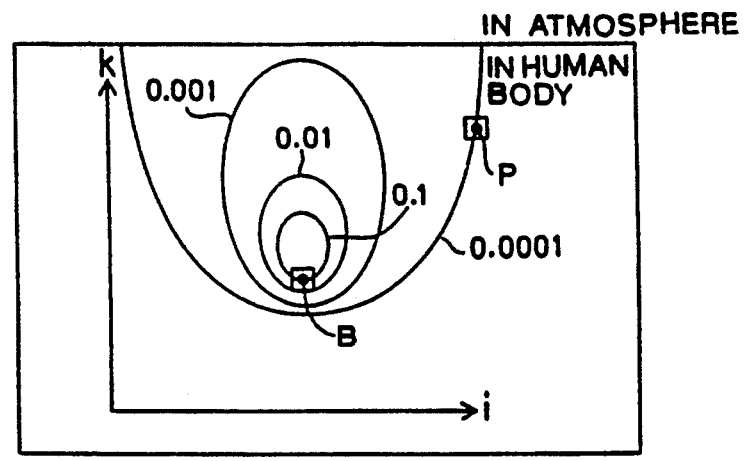
F I G. 18 (C)
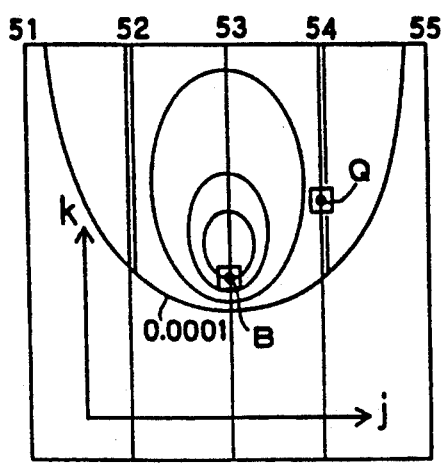
F I G. 18 (D)

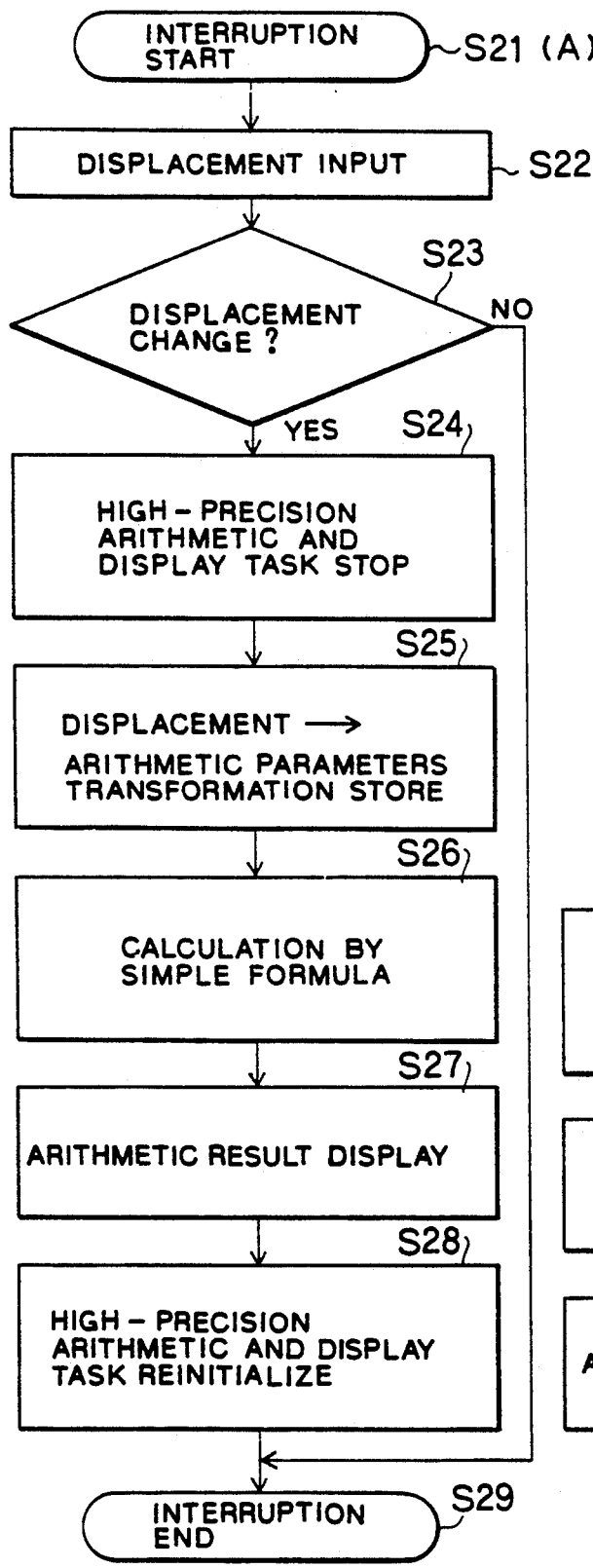
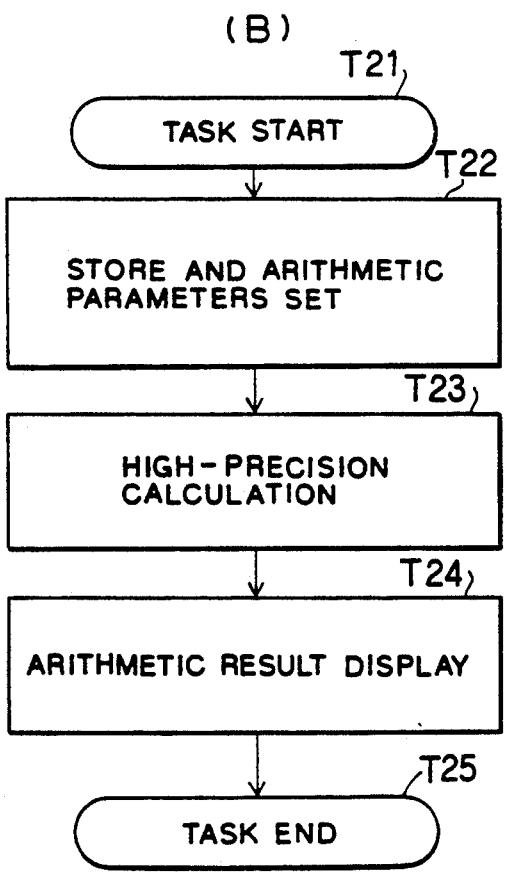
FIG. 20

RADIOTHERAPY TREATMENT PLANNING SYSTEM

BACKGROUND OF THE INVENTION

1. Field of the Invention

The present invention relates to a radiotherapy treatment planning system, so as to calculate the absorbed dose in an object to be irradiated, at radiotherapy with a medical linac and a cobalt-60 γ-ray irradiating system.

2. Description of the Prior Art

FIG. 1 is an explanatory view to represent how to irradiate a lesion of humans (an object to be irradiated) with X ray in order to perform X-ray treatment. In the figure, the numerical FIG. 30 represents an X-ray source (radiation source); 32, a patient (human body); 34, a lesion of the patient; 36, the X-ray beam width.

As is shown in FIG. 2, the most part of X-ray 38 incident to the human body 32 is scattered by Compton scattering. That is, X-ray 38 bombards the electrons in the atoms of the human body 32 (water holds its most part), and X-ray itself is concurrently scattered and becomes a scattered beam 42. Comparing with the energy of the initial X ray, the scattered beam 42 has a reduced energy, by the energy which is given to the electrons, leading to a phenomenon to lengthen the wave length. The scattered angle β of the electron beam 40 is then 90° or less.

The absorbed dose of the lesion 34 from X-ray irradiation (referred to as "dose" hereinafter) is in proportion with the number of ion pairs generated when the electron beam 40 passes the lesion 34. As is shown in FIG. 3, the process for the electron beam 40 incident to an observational region 44 in the lesion 34 consists of a direct process in which the electrons through a first Compton scattering is directly incident to the observational region 44, a first scattering in which the electrons generated at a second scattering of X ray are incident to the observational region 44, and a multiple scattering in which the electrons generated at more than triple scattering are incident to the observational region 44.

The treatment of a patient 32 with X ray 38, requires the information of the dose of a lesion 34. This is derived from the need to determine the dose of X ray 38 so as to cause necessary damage on the lesion 34. Therefore, there is a demand for a radiotherapy treatment planning system to execute dose calculation. For conventional radiotherapy treatment planning systems, the dose calculation has been performed by employing Monte Carlo technique, convolution method, delta-volumetric method, equivalent tissue air ratio (ETAR) technique, power law method, scatter air ratio technique or RTAR technique.

Monte Carlo technique, a process in which the three-dimensional calculation without approximation is iteratively carried out by means of simulation until a sufficient precision can be achieved, proposes the most accurate dose distribution, but it takes eight hours or longer even if 1MIPS computer is employed as a radiotherapy treatment planning system. In order to shorten such calculation time, according to the convolution method, the distribution of dose contribution to other points due to the occurrence of scattering at one point is preliminarily calculated, which calculation is then applied to the entire X-ray irradiated points to add up the individual distributions together, leading to the determination of dose distribution. According to delta-volumetric method, concerning a region of interest, X ray is divided into direct ray, a first scattered beam and other scattered beams, which are then integrally calculated in three dimension. On the contrary, by ETAR technique, the three-dimensional effects of scattered beam are introduced into a two-dimensional equivalent plane to perform two-dimensional integration. As is shown in FIG. 4, the power law method is a correction method applied for the case in which there are heterogeneous layers of densities $\rho_1$ and $\rho_2$ in a depth direction. The symbol 46 herein represents the observational point in the observational region 44. RTAR technique is a method utilizing the evidence that the absorbed dose becomes identical if the ratio of an area in an irradiated field to a circumferential length is identical, when viewed from the side of a source 30. SAR technique is a method searching SAR table, after converting the contribution of scattered beam into an equivalent irradiation field radius, based on the form of an irradiated field.

The radiotherapy treatment planning systems utilizing each of the methods described above are generally realized by employing computer programs. In performing each calculation, tomographic images by X-ray CT are widely used. From the density of the CT images, the electron density corresponding to the X-ray energy is calculated for use.

The radiotherapy treatment planning systems utilizing each of the methods mentioned hereinabove are described in detail in "Computer Application in Radiation Therapy Treatment Planning", Vol. 1, No. 2, James A. Purdy, 1983.

Since the conventional radiotherapy treatment planning systems are in such structure as has been described above, they have such problems as follows; those determining the contribution of scattered beam by three-dimensional calculation take too long calculation time to be applied in practical radiotherapy treatment; those determining the contribution of scattered beam by two-dimensional calculation cannot sufficiently compensate the heterogeneity in electron density and the deformation of an irradiated field, so that there has been suggested a problem about them such that there cannot be performed under all conceivable conditions the dose calculation to meet the ICRU (International Commission on Radiation Units and Measurements) recommendation, namely, that the error in an applied dose should be suppressed within 5% or less. In case that the ETAR method has been used, for example, the error exceeding 7% has occurred in some cases.

FIG. 5 shows a real-time dose distribution arithmetic and display system in the conventional radiotherapy treatment planning systems. In FIG. 5, the FIG. 101 represents a displacement input unit comprising a truck ball or a rotary switch, provided with a required potentiometer to transform the input from an operator to the system, into an electric signal corresponding to the input. 102 is a main arithmetic unit, comprising a digital computer of a required scale. 103 is a high-speed arithmetic unit comprising an array processor, to execute the required calculation of dose distribution at a high velocity. 104 is an image memory, to memorize the calculated results of dose distribution with the high-speed arithmetic unit 103, in order to display the results on desirable images. 105 is a character-display CRT and 106 is a key board, both of which perform the necessary functions as man-machine interface between an operator and the system. 107 is a graphic CRT, to display on its scope the contents stored in the image memory 104.

FIG. 6 is a flow chart to explain the operation of the system.

The operation of the above system will be now explained with reference to FIGS. 5 and 6.

A first step S400, push and press motion of a certain suitable start key (not shown in the figure) or the like will make start the real-time dose distribution arithmetic and display system.

At next step S401, the key board 106 as a man-machine interface proposes a preset arithmetic condition (arithmetic matrix, arithmetic precision, computing time and the like) through an operator. As an arithmetic precision, for example, either one of high-precision calculation and simple calculation is then selected. At step S402 following the above step, it is judged whether high-precision calculation is selected or not. When the result of such judgment is YES, the displacement is input at step S408, sequentially followed by the transformation of the displacement into arithmetic parameters (S409), the calculation based on a preset formula with high precision (S410) and the display of the results of such calculation (S411). The operation from steps S408 to S411 is carried out as follows. That is, a preset displacement is input through a displacement input unit 101 by an operator, which is then transformed into a suitable therapeutic parameter such as angle of the body of a therapeutic system, form of an irradiated field, form of shielding blocks and the like, by the subsequent main arithmetic unit 102. Through the character display CRT 105 and the key board 106 as man-machine interface, being in connection with the main arithmetic unit 102, an operator preliminarily determines a preset arithmetic condition (arithmetic matrix, arithmetic precision, computing time and the like). The high-speed arithmetic unit 103 executes the required calculation by using the preset arithmetic formula for calculating dose distribution (a high-precision formula herein), on the basis of the arithmetic condition described above. The dose distribution data obtained as the results of the calculation is loaded into the image memory 104 at the subsequent step. By executing such operation on real time, the dose distribution based on the preset parameters is displayed on the graphic CRT 107. After the display is done, the initial step S401 is resumed.

Alternatively, when the result of the judgment at step S402 is NO, displacement is input at step S403, followed by the transformation of the displacement into calculating parameters (S404), the calculation based on a preset simple formula (S405) and the display of the results of such calculation (S406). At the subsequent step (S407), the judgment is done concerning whether or not real-time processing is completed. When the result of the judgement is NO, return to step S403 and then the processing of the following steps is repeated. On the contrary, when the result of the judgment at the above step S407 is YES, return to the initial step S401. The operation from the steps S403 to S406 is the same as the operation from the aforementioned steps S408 to S411, except the calculation by the simple formula. The detailed explanation is therefore not recited herein.

In the conventional real-time arithmetic result display system in such structure as described above, the arithmetic condition is preliminarily set by an operator, and the system realizes real-time (calculation) display based on a preset displacement input. In the conventional system, real-time display using an arithmetic formula with a high speed but with a low precision (in other words, for example, smaller arithmetic matrix) is generally done, while an operator searches the optimum parameters while appropriately changing input displacement. Consequently, real-time (calculation) display with a high-precision formula (in other words, larger arithmetic matrix) is executed, by using the optimum parameters searched. There has been suggested such a problem that it becomes extremely complex the work to optimize therapeutical parameters under a high-precision condition (in other words, larger arithmetic matrix) which is necessary for an operator.

SUMMARY OF THE INVENTION

The present invention is carried out in order to solve the problems described above, which is intended to provide a radiotherapy treatment planning system to enable the shortening of the computing time until it reaches a practical time period, while suppressing to the minimum the error contained in the calculated dose to its actual dose.

Furthermore, the objective of the present invention is to provide a real-time arithmetic result display system to be applied to a radiotherapy treatment planning system. In the display system, therapeutical parameters can be optimized under a high-precision condition (namely, larger arithmetic matrix) actually required for an operator. The display system does not need such complex operation for switching the arithmetic condition.

The radiotherapy treatment planning system according to the present invention is provided with a distribution of contribution output unit for outputting the distribution of contribution, in an object to be irradiated, representing the distribution of contribution rates of scattered radiation to an observational point, and an arithmetic unit for determining the absorbed dose at the observational point due to scattered radiation, by adding up those output contribution rates from the distribution of contribution output unit, multiplied by the electron densities at the individual points corresponding to the contribution rates.

The distribution of contribution output unit described above enables the reduction in the number of arithmetic process at the arithmetic unit, by correcting the distribution of contribution in the direction from the observational point leading to a radiation source, with the electron density corrected length between them, thereby giving the information concerning the distribution of contribution after the correction, to the arithmetic unit.

Or, the radiotherapy treatment planning system according to the present invention is provided with a distribution of contribution output unit for outputting the distribution of contribution, in an object to be irradiated, representing the distribution of contribution rates of generated electron beam to an observational point, a subject setting unit for defining a subject region as the region where the observational point is present in the range the electron beam from other points can reach, and an arithmetic unit for determining the absorbed dose at the observational point due to scattered electron beam, by adding up those contribution rates of the electron beam at individual points within the region determined by the subject setting part, multiplied by the electron densities at the individual points corresponding to the contribution rates.

The subject setting unit determines other points from which scattered electron beam reaches an observational point, as the arithmetic subject region, and the other points excluding the above points as the non-subject region.

The radiotherapy treatment planning system according to the present invention is provided with a distribution of contribution data unit for outputting the distribution of contribution, in an object to be irradiated, representing the distribution of contribution rates of scattered radiation or electron beam generated from scattering to an observational point, a subject-region determining unit for determining the region in the object to be irradiated, where the distribution of contribution exceeds a preset contribution rate, and for determining the arithmetic matrix size concerning the region, and an arithmetic unit for determining the absorbed dose at the observational point due to scattered radiation or electron beam, by adding up those contribution rates of the scattered radiation or the electron beam at individual points within the region determined by the subject-region setting unit, multiplied by the electron densities at the individual points.

The aforementioned subject-region determining unit determines a region where the distribution of contribution of scattered radiation or electron beam to an observational point exceeds a preset contribution rate, and inputs the region as the arithmetic subject region to the arithmetic unit. The subject-region determining unit optimizes the arithmetic efficiency by rendering the arithmetic matrix size changeable, depending on the slope of the distribution of contribution.

The real time arithmetic result display system suitable for a radiotherapy treatment planning system, according to the present invention, is provided with a displacement input unit, a first arithmetic unit for executing the calculation based on a preset high-precision formula when no change is observed in the displacement, a second arithmetic unit for executing the calculation based on a preset simple formula when any change is observed in the displacement, and a display system for displaying the arithmetic results by the first or second arithmetic unit, which is characterized in that the calculation with a high precision is constantly performed by the first arithmetic unit, and the calculation using the high-precision formula by the first arithmetic unit is interrupted when change is observed in the displacement, to execute the calculation using a simple formula by the second arithmetic unit.

The calculation with a high precision is constantly performed by the first arithmetic unit, and the calculation using the high-precision formula by the first arithmetic unit is interrupted when any change is observed in the displacement, to execute the calculation using a simple formula by the second arithmetic unit.

BRIEF DESCRIPTION OF THE DRAWINGS

FIG. 17 is a block diagram to show the radiotherapy treatment planning system according to still another embodiment of the present invention.

FIG. 18a, b, c, d, a distribution pattern showing three-dimensional distribution of contribution.

FIG. 19 is a block diagram to show a real-time arithmetic result display system, according to an embodiment of the present invention.

FIG. 20 is a flow chart representing the operation of the system shown in FIG. 19.

DETAILED DESCRIPTION OF THE PREFERRED EMBODIMENTS

Figure 1:
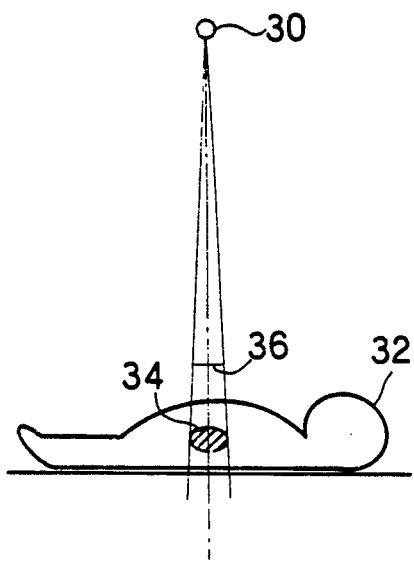
FIG. 1 is an explanatory view how X ray irradiates human body.
Figure 2:
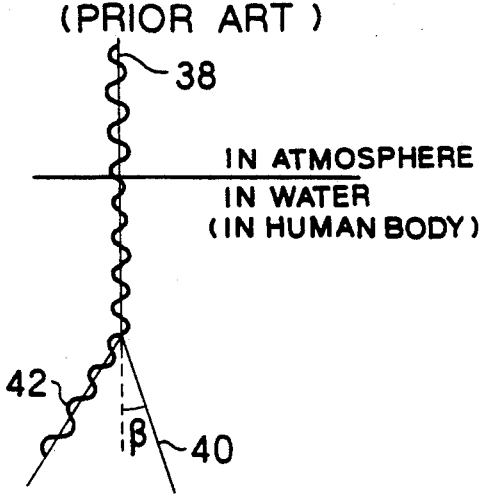
FIG. 2 is an explanatory view to show the state of Compton scattering.
Figure 3:
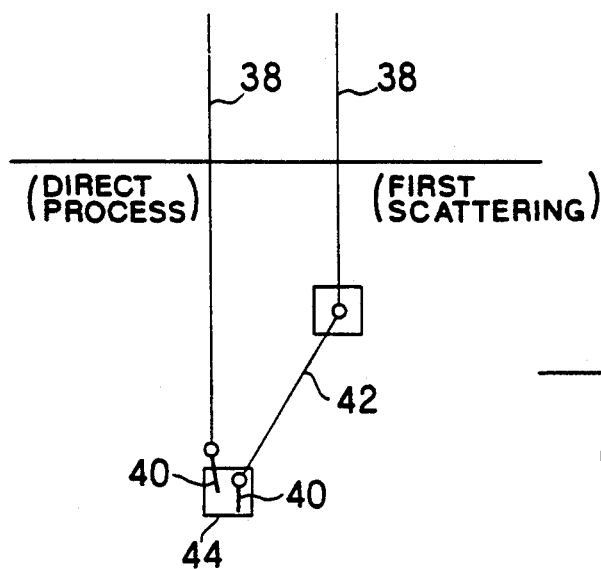
FIG. 3 is an explanatory view to explain the process of scattering.
Figure 4:
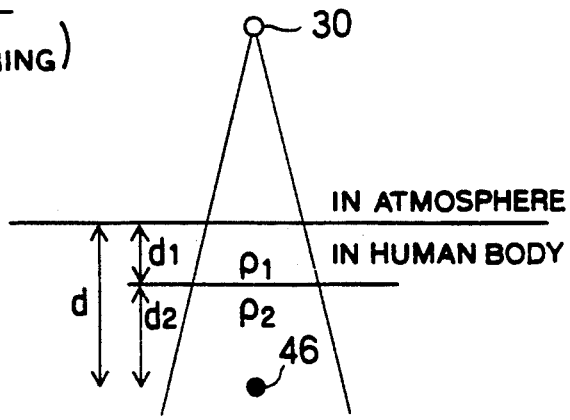
FIG. 4 is an explanatory view to represent the heterogeneity of electron density in a depth direction.
Figure 5:
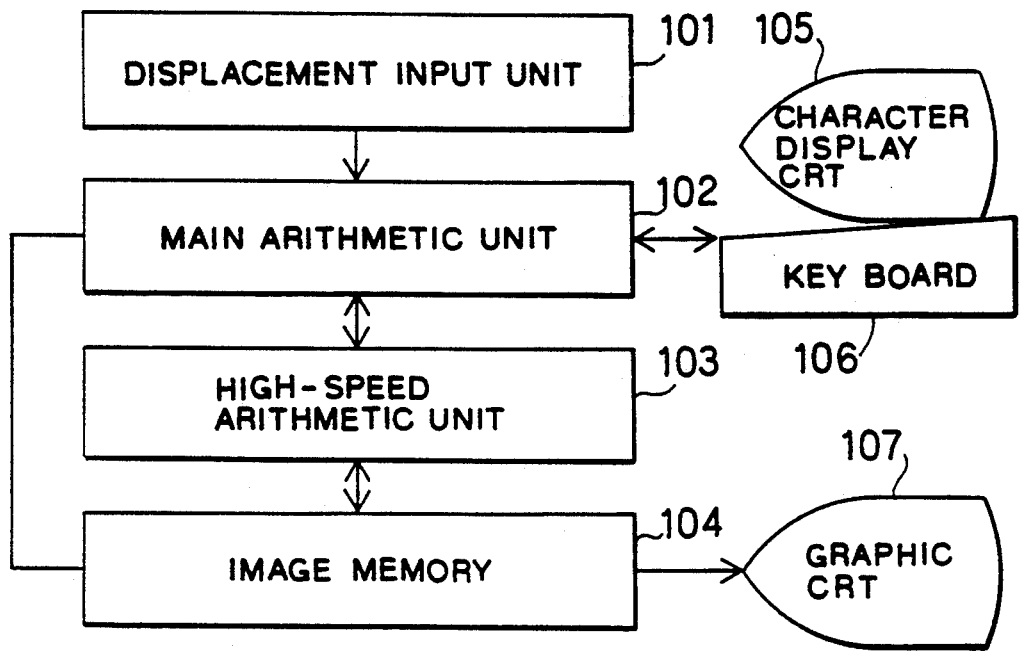
FIG. 5 is a block diagram to show the conventional real-time arithmetic result display system.
Figure 7:
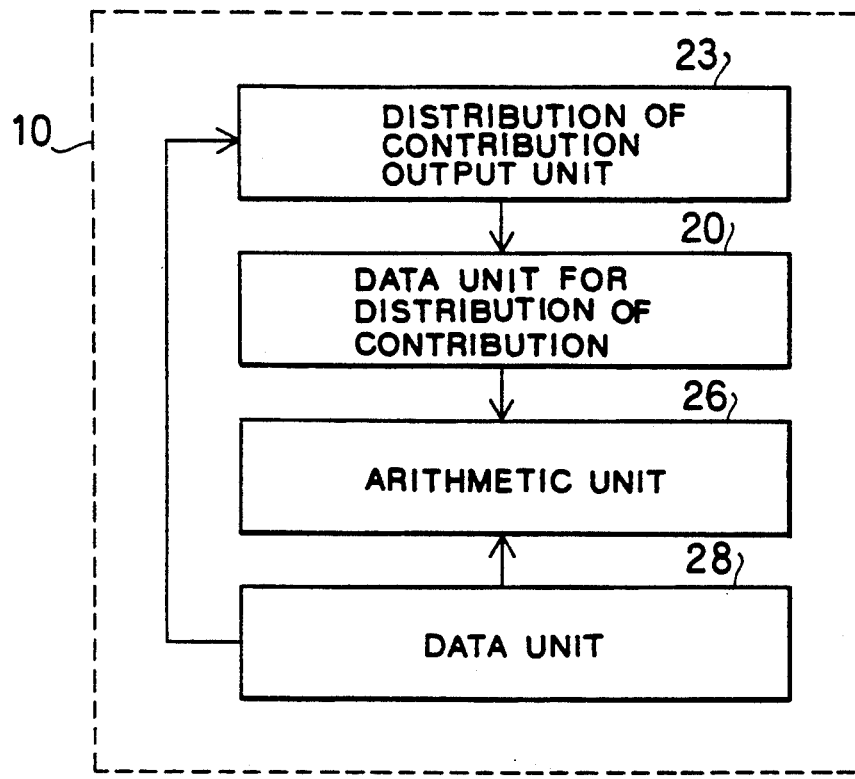
FIG. 7 is a block diagram to show a radiotherapy treatment planning system, according to an embodiment of the present invention.
Figure 6:
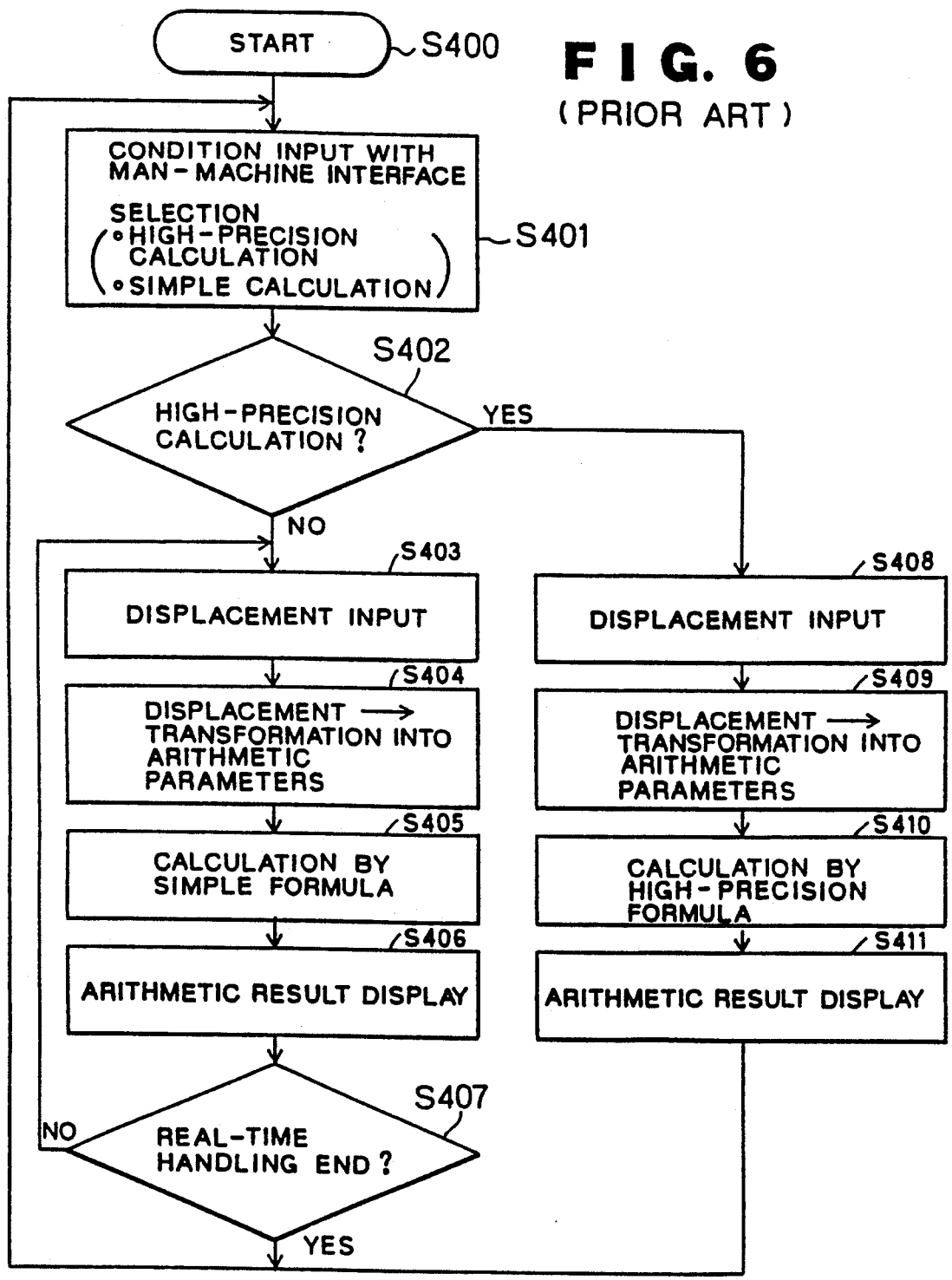
FIG. 6 is a flow chart to show the operation of the system as is shown in FIG. 5.

A preferred embodiment of the present invention will now be explained in detail referring to the accompanying drawings hereinafter. In FIG. 7, 10 represents a radiotherapy treatment planning system; 20, a data unit for distribution of contribution in which the contribution rate of the X ray scattered at each point in a human body 32 to an observational point 46 is loaded; 23, a distribution of contribution output unit for outputting the distribution of contribution corrected with the electron density corrected length employing the distribution of electron density; 26, an arithmetic unit for calculating the dose due to the scattered beam, based on the output distribution of contribution and the electron density at each point; 28, a data unit in which the electron density and the like at each point are loaded. The distribution of contribution to be loaded in the data unit for distribution of contribution 20 can be determined by experiments, other than calculation.

Figure 8:
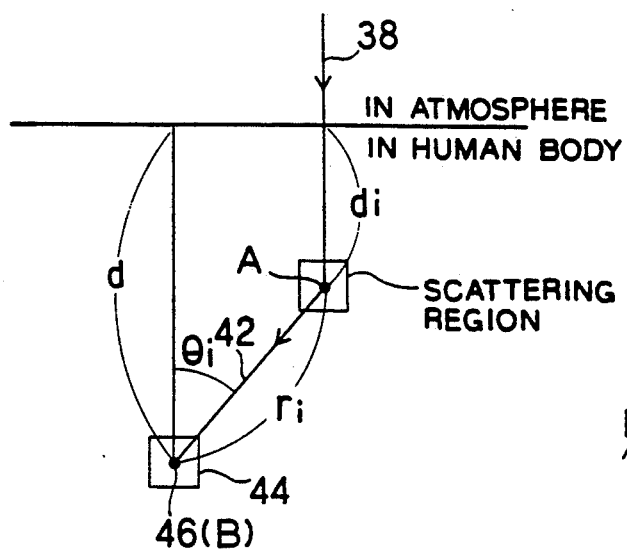
FIG. 8 is an explanatory view to represent the relationship between incident X ray and scattered X ray.

Next, operation of this system will now be explained. FIG. 8 shows how X ray 38 is incident to an X-ray absorbable body such as human body, followed by scattering at point A (scattering point), to be incident to the observational point 46. The observational point 46 is referred to as point B hereinafter. The rate of the scattered beam 42 contributing to the point B (contribution rate), among the scattered X ray, can be represented in the following formula:

$$\eta_x(d, \theta_i, r_i) = \exp(-\mu_1 d_i) \cdot f(\theta_i) \cdot \frac{\exp(-\mu_2 r_i)}{r_i^2} \cdot C \quad (1)$$

[wherein, $\mu_i$ is the mean X-ray absorption coefficient; $f(\theta)$ is a probability of Compton scattering of X ray at an angle of $\theta$; and C is a coefficient]. The formula can also be rewritten as follows;

$$\eta_x(d, \theta_i, r_i) = C \cdot \frac{f(\theta_i)}{r_i^2} \cdot \exp(-\mu_1 d_i - \mu_2 r_i) \quad (2)$$

If $\mu_1 = \mu_2$, namely, if the absorption coefficient is constant within the human body, the following formula is established;

$$\begin{aligned}-\mu_1 d_i - \mu_2 r_i &= -\mu(d_i + r_i) \\ &= -\mu\{d + r_i(1 - \cos\theta_i)\}\end{aligned} \quad (2a)$$

For example, if $\mu = 0.03/\text{cm}$, $r_i = 7$ cm and $\theta = 25°$ provided that X ray 38 of 4MV is employed, $\exp\{-r_i(1-\cos\theta)\} = 0.98$; if the value of $\theta$ is smaller, the error from the formula (1) is 2% or less even if $-\mu d_i - \mu r_i \approx -\mu d$. If the value of $\theta$ is even smaller, the error gets much smaller. Then, $$\eta_x(d, \theta_i, r_i) = C \cdot \frac{f(\theta_i)}{r_i^2} \cdot \exp(-\mu d) \quad (3)$$

Figure 9:
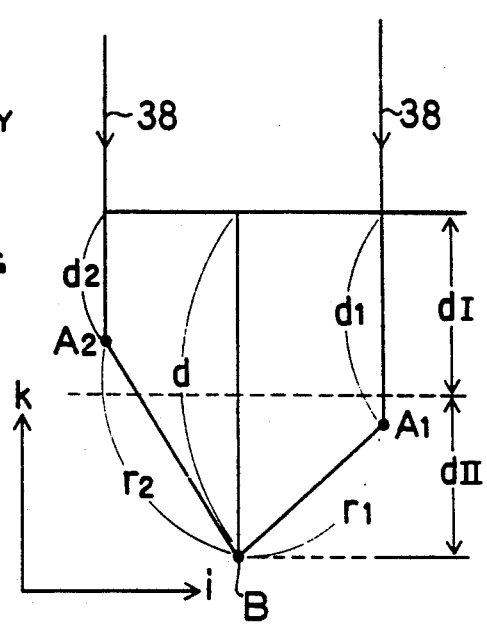
FIG. 9 is an explanatory view to show the heterogeneity of electron density.

Next, the case of $\mu_1 \neq \mu_2$, namely, the case where the absorption coefficient is heterogeneous in the depth direction will be explained with reference to FIG. 9. The contribution rate of $A_1$ is represented as follows;

$$\begin{aligned}\eta_x(d, \theta_1, r_1) &= C \cdot \frac{f(\theta_1)}{r_1^2} \cdot \exp\{-\mu_1 d_I - \mu_2(d_1 - d_I) - \mu_2 r_1\} \\ &= C \cdot \frac{f(\theta_1)}{r_1^2} \cdot \exp\{-\mu_1 d_I - \mu_2 d_{II} - \mu_2 r_1(1 - \cos\theta_1)\}\end{aligned} \quad (4)$$

As the absorption coefficient is nearly in proportion with the electron density $\rho$ in a human body, the following formula is established;

$$-\mu_1 d_I - \mu_2 d_{II} \approx -\mu(\rho_1 d_I + \rho_2 d_{II}) = -\mu \tilde{d} \quad (5)$$

[wherein $\tilde{d}$ is the electron density corrected length of the depth of human body to the point B in the direction of a source]. Generally (in case that the heterogeneity is seen over more multiple layers), $\tilde{d} = _N\Sigma\rho_N d_N$ (N=I, II, III, ...). From the formulas (4) and (5), the formula below is obtained:

$$\eta_x(d, \theta_1, r_1) = C \cdot \frac{f(\theta_1)}{r_1^2} \cdot \exp\{-\mu \tilde{d} - \mu_2 r_1(1 - \cos\theta_1)\} \quad (6)$$

Hence, in case of $\theta < 25°$, $$\eta_x(d, \theta_1, r_1) \approx C \cdot \frac{f(\theta_1)}{r_1^2} \cdot \exp(-\mu \tilde{d}) \quad (7)$$

Herein, the formula (7) is the contribution rate through the point $A_1$.

The contribution rate through the point $A_2$, is considered hereinbelow;

$$\eta_x(d, \theta_2, r_2) = C \cdot \frac{f(\theta_2)}{r_2^2} \cdot \quad (8)$$

-continued $$\exp\left(-\mu_1 d_2 - \frac{\mu_1(d_I - d_2)}{\cos\theta_2} - \frac{\mu_2 d_{II}}{\cos\theta_2}\right)$$

wherein $$\begin{aligned}&-\mu_1 d_2 - \frac{\mu_1(d_I - d_2)}{\cos\theta_2} - \frac{\mu_2 d_{II}}{\cos\theta_2} = \\ &\quad -\mu_1 d_I - \mu_2 d_{II} - \mu_1(d_I - d_2)\left(\frac{1}{\cos\theta_2} - 1\right) - \\ &\quad \mu_2 d_{II}\left(\frac{1}{\cos\theta_2} - 1\right) = \\ &\quad -\mu_0 \tilde{d} - \{\mu_1(d_I - d_2) + \mu_2 d_{II}\}\left(\frac{1}{\cos\theta_2} - 1\right)\end{aligned}$$

thus, $$\eta_x(d, \theta_2, r_2) = C \cdot \frac{f(\theta_2)}{r_2^2} \cdot \exp\{-\mu \tilde{d} - \mu \tilde{r}(1 - \cos\theta_2)\} \quad (9)$$

[wherein generally $\tilde{r} = _N\Sigma\rho_N r_N$.] The formula (9) is also established as follows, in case of $\theta < 25°$;

$$\eta_x(d, \theta_2, r_2) \approx C \cdot \frac{f(\theta_2)}{r_2^2} \cdot \exp(-\mu \tilde{d}) \quad (10)$$

So, the formulas (6) and (9) are generally represented as follows;

$$\eta_x(\tilde{d}, \theta_i, r_i) = C \cdot \frac{f(\theta_i)}{r_i^2} \cdot \exp\{-\mu \tilde{d} - \mu \tilde{r}(1 - \cos\theta_i)\} \quad (11)$$

In case of $\theta_i < 25°$, $$\eta_x(d, \theta_i, r_i) \approx C \cdot \frac{f(\theta_i)}{r_i^2} \cdot \exp(-\mu \tilde{d}) \quad (12)$$

As has been described above, the distribution of contribution output unit 23 may output the corrected distribution of contribution {corresponding to the formula (11)} after the correction with the electron density corrected length is carried out by employing the density of a human body 32.

As the calculation for calculating the dose due to the scattered beam at the point B, the arithmetic unit 26 may perform the calculation based on the following formula;

$$D_{sb} = _i\Sigma_j\Sigma_k\Sigma\rho(i,j,k) \rho_{xb}(i,j,k) \quad (13)$$

[wherein $\rho(i,j,k)$ is the electron density of each part obtained by equally dividing the arithmetic region, the density being represented on the coordinate (i,j,k), while $\eta_{xb}(i,j,k)$ is obtained by applying each of those represented by the formula (11) to the individual parts.]. The values of $\rho(i,j,k)$ is preliminarily loaded in the data unit 28. In the actual dose calculation, the inverse square correction with the distance from a source and the dose ratio outside the axis from k axis, are taken into account so as to correct the beam width as is shown in FIG. 18(A). But these are not directly related to the present invention, so the explanation about them is omitted.

Figure 10:
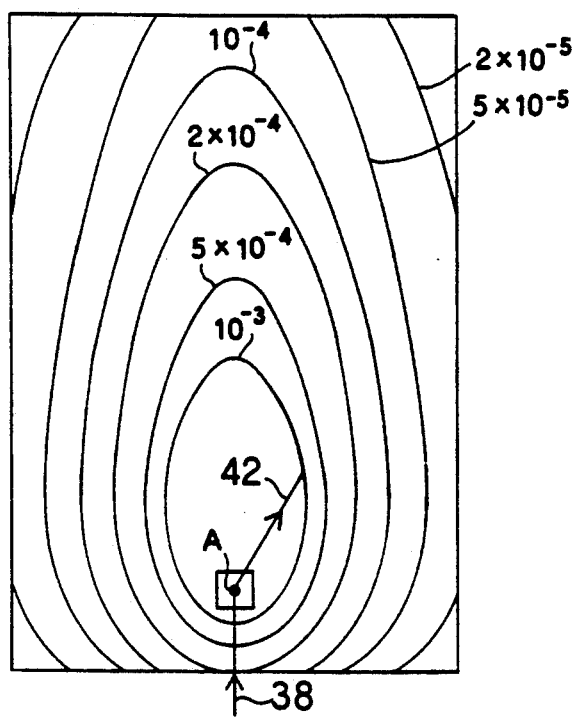
FIG. 10 is an equivalent dose diagram representing the distribution of scattered X ray.

As the X-ray scattering distribution [f(θ)] by Compton scattering is focused on the frontal face if the X-ray energy is 4 MV or more, as is shown in FIG. 10, f(θ) is smaller at the part where r is larger provided that θ is large. Therefore, the effect of the term $\exp\{\mu \tilde{r}_i(1-\cos\theta_i)\}$ is small, so that the formula (12) may be applied to such part. At the arithmetic unit 26, measuring or calculating the value of $$C \cdot \frac{f(\theta_i)}{r_i^2}$$

regarding each matrix (i,j,k) is only needed, to obtain $\eta_{xb}$ by multiplying the value with $\exp(-\mu\tilde{d})$ or $\exp\{-\mu\tilde{d}-\mu\tilde{r}_i(1-\cos\theta_i)\}$. Here, if the measured value is used, effect of multiple scattering can influence $\eta_{xb}$.

Because the calculation by the formula (11) in which the value of $$C \cdot \frac{f(\theta_i)}{r_i^2}$$

is preliminary determined is much more simplified compared with the formula (1), and is also the speediest and easiest calculation to an electronic computer, the computing time is shortened about one-tenth the time necessary for the conventional one, in case that general electronic computers are applied to a radiotherapy treatment planning system. In the conventional radiotherapy treatment planning system, the calculation by the formula (1) or terms of multiple scattering corresponding to the formula (1) is to be executed concerning the entire region. The arithmetic unit 26 executes three-dimensional calculation, but the process described above can be applied to two-dimensional calculation.

Figure 11:
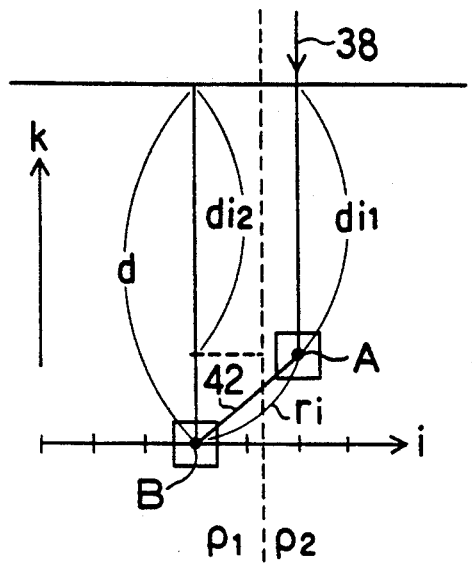
FIG. 11 is an explanatory view to show the heterogeneity of electron density in a transverse direction.

As is shown in FIG. 11, the i-directional heterogeneity of the electron densities $\rho_1$ and $\rho_2$ can be also present. In order to correct the heterogeneity the correction may be performed on the formula (12). That is, it may be multiplied by the following formula;

$$\exp\{-\mu(\tilde{d}_{i1}-\tilde{d}_{i2})\} \tag{14}$$

In that case, however, an error may develop when X ray is incident slantingly, but the error at a point with a large contribution rate (a point closer to the point B)

When the value of θ is small, the following formula is established;

$$\eta_x(\tilde{d}, \theta_i, r_i) = C \cdot \frac{f(\theta_i)}{r_i^2} \cdot \exp(-\mu\tilde{d}) \cdot \tag{15}$$

$$\exp\{-\mu[(\tilde{d}_i - d_i) + (\tilde{r}_i - r_i)]\}$$

Then, approximation can be done in the subsequent formula;

$$\exp\{-\mu[(\tilde{d}_i-d_i)+(\tilde{r}_i-r_i)]\} \approx 1-\mu\{(\tilde{d}_i-d_i)+(\tilde{r}_i-r_i)\} \tag{16}$$

or $$\exp\{-\mu(\tilde{d}_i - d_i + \tilde{r}_i - r_i)\} \approx \tag{17}$$

$$\exp\{-\mu(\tilde{d} - d + \tilde{d}_{i1} - \tilde{d}_{i2})\} \approx 1 - \mu(\tilde{d} - d + \tilde{d}_{i1} - \tilde{d}_{i2})$$

By such manner, the arithmetic time can be more shortened. In case that such approximation can be done, the error is less than 1% at an actual condition, which is practical enough. As the calculations by formula (16) and (17) under fixed point can be carried out, resulting in calculation is obtained in high speed. When ETAR technique or the like is used, calculation under floating point is required. The term $\tilde{r}_i$ in the formula (16) can be given by $$\tilde{r}_i = \beta \Sigma_j \Sigma_k \Sigma \rho(i,j,k) \frac{d(i,j,k)}{\cos\theta_i}$$

but the arithmetic time gets longer in that case. The size of a box-shaped element is represented by d(i,j,k). Therefore, the term $r_i$ may be approximated as follows;

$$\tilde{r}_i \approx \frac{\rho_a + \rho_b}{2} \cdot r_i \tag{18}$$

[wherein $r_i$ may be preliminarily calculated, corresponding to each matrix].

Since the radiotherapy treatment planning system is in a composition comprising calculating the contribution rate of scattered beam by using the electron density corrected length and calculating the dose by using the contribution rate and the electron density distribution, as has been described above, there are obtained the effects to output the dose in a short time while maintaining the high precision.

Figure 12:
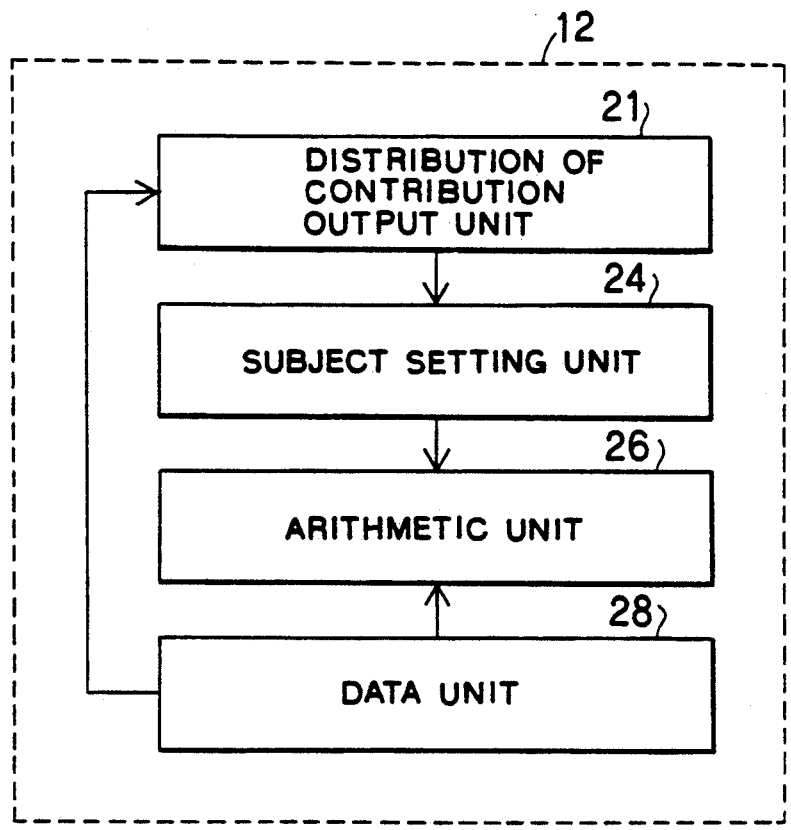
FIG. 12 is a block diagram to show the radiotherapy treatment planning system according to another embodiment of the present invention.

FIG. 12 is a block diagram to show the radiotherapy treatment planning system by another embodiment of the present invention.

In FIG. 12, the numerical FIG. 12 represents a radiotherapy treatment planning system; 21 is a distribution of contribution output unit outputting the distribution of contribution representing the contribution rate such that the electron beam (direct ray) generated at each point, among the points in a human body and irradiated with X ray, contributes to the point B; 24 is a subject setting unit for determining the boundary, in the individual points, between the points from which X ray can reach the point B and the points from which X ray cannot reach the point B, thereby determining an arithmetic subject region; 26 is an arithmetic unit for calculating the dose of the subject region due to the direct ray, from the distribution of contribution and the electron density of each part; 28 is a data unit which contains the electron density and the like of each point.

Figure 13:
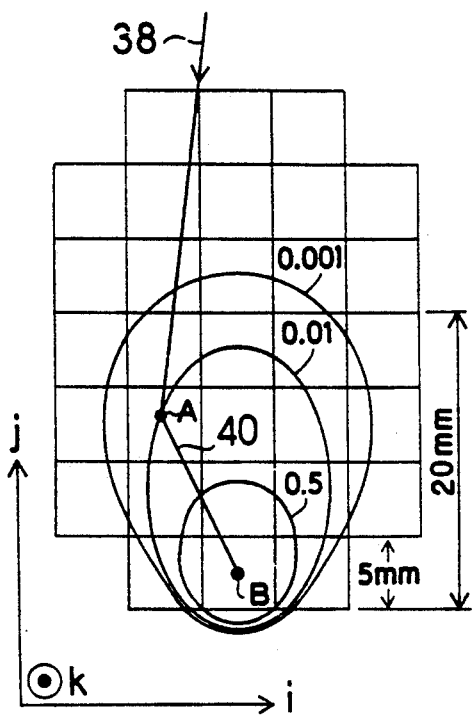
FIG. 13 is an explanatory view to show how to divide an object to be irradiated into multiple regions.

The operation is explained hereinbelow. FIG. 13 is an example of equally dividing a human body 32 into each 5 mm cube. The electron beam runs to the point B while it is winding actually by multiple scattering, but the path of the electron beam is straight in FIG. 13 as it is simplified. The contour line in the figure represents the line on which the contribution rate $\eta_e$ of the electron beam to the point B is equal. Provided that incident X ray 38 is scattered at the point A with the contribution rate $\eta_e=0.01$, the electron beam incident to the point B is given by the following formula;

$$\rho_a \cdot \rho_e \cdot 0.01 \rho_a$$

if the electron density at the point A is $\rho_a$. Hence, the dose $D_{eb}$ at the observational region including the point B (B region), due to the entire electron beams (entire direct rays), is given by the formula below;

$$D_{eb} = i\rho_j \Sigma_k \rho(i,j,k) \rho_{eb}(i,j,k) \quad (19)$$

[wherein $\rho(i,j,k)$ is the electron density of a cube, represented on the coordinate (i,j,k); and $\eta_{eb}(i,j,k)$ is the contribution rate of the electron beam from the cube (i,j,k) to the region B.

Figure 14:
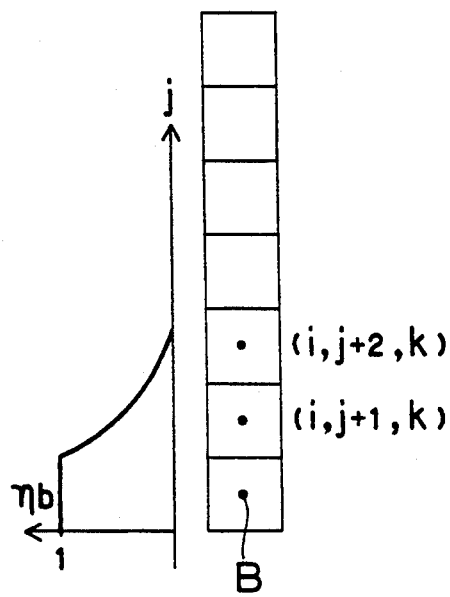
FIG. 14 is an explanatory view to represent the change in contribution rate.

The addition by the formula (19) is to be sufficiently carried out if it is performed only for the region $\eta_e$-(i,j,k)>0.001. The reason is that the electron beam has a preset range (the range of electron's reach) as shown in FIG. 14 and the contribution of the points, outside such points as they are $\eta_e$<0.01, disappears.

The distribution of contribution of the electron beam in the human body 32 changes, depending on the electron density $\rho$. The distribution of contribution in a real human body 32 is nearly determined, particularly by the electron densities in the region B and in the following cubes to the source direction therefrom. Thus, the preliminary determination of the correlation between the $\eta_e$ distribution and the distribution of $\rho(i,j,k)$ can yield the $\eta_e$ distribution. The change in the $\rho(i,j,k)$ distribution in the j-direction is enough to predict $\eta_e$ approximately.

The distribution of $\rho(i,j,k)$, namely the distribution of electron density, is therefore loaded in the data unit 28, together with the electron-density-corresponding contribution rate of the electron beam. Based on the distribution of the electron density in the j-direction and the electron-density-corresponding contribution rate of the electron beam, the subject setting unit 24 determines the range of a distribution of $\rho(i,j,k)$ to be employed as subject, on considering the arithmetic precision and computing time, necessary for the arithmetic unit 26. The range may be within the range of electron beam's reach. As the range of electron beam's reach is about 3 cm in case that it is Compton electron beam generated by 6 MV X-ray, the range is smaller than a region which the system treats, for example, 20 to 40 cm box size. By determining the arithmetic subject region for the arithmetic unit 26, the computing time at the arithmetic unit 26 can be further shortened.

Figure 15:
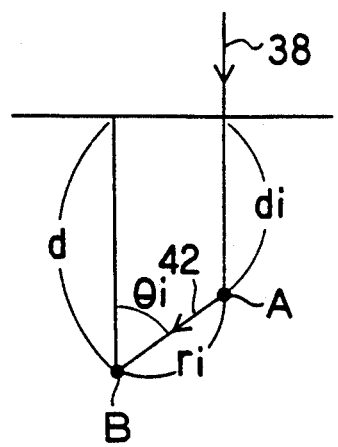
FIG. 15 is an explanatory view to show the state of X-ray scattering.

The contribution rate of electron beam can be represented by the formula;

$$\eta_e = \exp(-\mu \tilde{d}_i) \cdot \frac{C}{r_i^2} \cdot g[\bar{r}, R(E)] \cdot f_e(\theta_i) \quad (20)$$

provided that X ray is scattered at the point A as is shown in FIG. 15. The symbol $\tilde{d}$ represents the electron density corrected length along $d_i$ previously described, and the formula; $\tilde{d} = \Sigma d_i \rho_i \cdot g[\bar{r}_i, R(E)]$ is a range function, determined by the range R(E) when the X-ray energy is E as well as by the electron density corrected length along $d_i$, $\bar{r}(\bar{r} = _i\Sigma r_i \rho_i)$ aforementioned and $f_e(\theta)$ is a probability of electron beam being scattered at the angle $\theta$.

Thus, the system can be structured such that $\eta_e$ can be determined, only by preliminarily measuring or calculating the term $$\frac{C}{r_i^2} \cdot f_e(\theta_i)$$

in the formula (20) and assigning it to cube (i,j,k), and further calculating $\tilde{d}$ of each cube (i,j,k) and making it into a table, and picking up individual data from the table to calculate $\bar{r}$.

As a method for determining a subject region, $\rho_i$ each is summed up from the point B toward the direction of a radiation source 30, to the point where the sum thereof reaches the range R(E), and the region including all of the above points can be defined as a subject region. Several kinds of $\eta_e$ may preferably be prepared, depending on X-ray energy E and the value of electron density The $\eta_e$ distribution is determined by $g[\bar{r}, R(E)]$ at the part where $\theta$ is small, while it is determined by $f_e(\theta_i)$ where $\theta_i$ is large. Therefore, the change in the electron density can bring about effects on the part with smaller $\theta_i$. It can be said thus that the determining method hereinabove described can yield good approximation.

Figure 16:
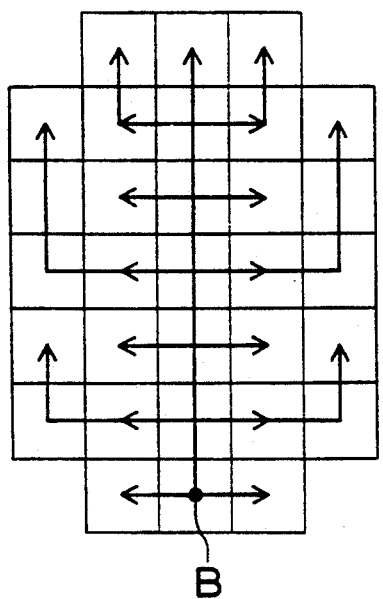
FIG. 16 is an explanatory view to show the direction of addition.

As is shown in FIG. 16, it may be established a composition comprising summing each electron density following the sequence preliminarily determined to achieve the range R(E), thereby determining $\bar{r}$, and simultaneously determining the weighing factor $W_b(i,j,k)$ of each cube (i,j,k) to the point B, and calculating the formula; $\rho_T = i\rho_j \Sigma_k \Sigma \rho(i,j,k) W_b(i,j,k)$, to determine $\eta_e$ corresponding to $\rho_T$, or to directly determine $\eta_e$.

When determining $\eta_e$ in the formula (20), the formula $$\bar{r} \approx \frac{\rho_a + \rho_b}{2} r_i$$

is used. The size of each of the cubes corresponding to $\rho_a$ and $\rho_b$ should be assumed rather large. Thus, the value of $\bar{r}$ can be calculated in a short time. The method can be used not only for X-ray irradiation but also for dose calculation at the irradiation of electron beam.

Since the radiotherapy treatment planning system is structured so that the dose of the region within the range of electron beam might be calculated by using the contribution rate and the electron density distribution, there is obtained the effect of outputting the dose for a short time while maintaining the high precision.

In the conventional system, the electron beam (direct beam) is treated by convolution method or Monte Carlo technique, that is, the dose of the observational point is determined by adding electron beams, each of which extends from scattering point, every scattering point. Consequently, it is impossible that the determining the object region or the calculation at every observational point makes a process higher in the conventional system.

FIG. 17 is a block diagram to show the radiotherapy treatment planning system by still another embodiment of the present invention.

In FIG. 17, the numerical FIG. 14 represents a radiotherapy treatment planning system; 22 is a data unit for distribution of contribution in which there is loaded the distribution of contribution representing the contribution rate that the scattered beam at each of the X-ray irradiated points among the part in a human body contributes to the point B or the contribution rate that the direct beam from each point contributes to the point B; 25 is a subject-region determining unit for determining the boundary, in the individual points, between the points in which the individual contribution rates exceed a preset value and the points in which they do not, thereby determining a subject region within the boundary and determining the spatial arithmetic matrix size; 26 is an arithmetic unit for calculating the dose of the subject region due to the scattered beam or the direct ray, based on the distribution of contribution and the electron density of each part; 28 is a data unit in which the electron density and the like of each point are loaded.

Next, operation will now be explained hereinbelow. FIG. 18 represents the contour line in three dimension, showing the distribution of contribution of scattered beam 42 or electron beam 40 to the point B. In the figure, the points P and Q independently represent the identical point. As is clearly shown in the figure, each point having the same distance from the point B on i-j plane has the same contribution rate to the point B. In the direction k, only the points above the point B have higher contribution rates. The figure shows the case where the electron density is homogeneous; in case that the electron density shows heterogeneous distribution, the distribution of contribution is more or less different from the distribution shown in FIG. 18. The numerical figures are only shown for explanation, and are not quantitatively accurate.

In such case, a subject region determining unit 25 determines a region with a higher contribution rate, based on the density on CT image (shown as slices 51 to 55 in FIG. 18$b$). For example, a region with a contribution rate $\theta_b$ exceeding 0.001 may be determined. In FIG. 18$b$, the region between the double lines of slices 52 and 54 corresponds to a subject region. An arithmetic unit 26 is provided with contribution data by the data unit for distribution of contribution 22, is provided with electron density by a data unit 28, and carries out multiplication of those corresponding to the region determined by the subject region determining unit 25 and sums up the results to output dose $D_b$. A subject region is generally divided into smaller regions, namely (i,j,k) regions, to perform calculation [(i,j,k) represents coordinate, i, j and k being natural numbers.]. Thus, calculation is carried out as follows;

$$D_b = {}_i\Sigma_j\Sigma_k\Sigma \rho(i,j,k)\, \rho_b(i,j,k) \qquad (21)$$

[wherein $\rho(i,j,k)$ is the electron density in the region (i,j,k); $\eta_b(i,j,k)$ is the contribution rate of the region (i,j,k).]

$$[\eta_b(i,j,k) = \eta_{xb}(k,j,k) + \eta_{eb}(i,j,k)]$$

The region satisfying the formula;

$$\eta_b(i,j,k) \geq 0.001$$

is the arithmetic subject. Conventionally, calculation is carried out on the entire regions enclosed by frames in (B), (C) and (D) of FIG. 18. The density of the region between the slices 52 and 54 can be determined by interpolation. By restricting the subject region as is described, computing time can be shortened even if three-dimensional calculation is done.

The contribution of other slices 52 and 54 may be introduced into the slice 53 containing the point B [which contribution is shown in dotted line in FIG. 18(B)]j The dose $D_{bN}$ due to slice N (N is a slice number) is determined as follows;

$$D_{bN} = {}_i\Sigma_j\Sigma_k\Sigma \rho(i,j,k)\, \eta_b(i,j,k) \qquad (22)$$

[wherein (i,j,k) is the region on the slice N]. $D_b$ is then determined as follows;

$$D_b = {}_N\Sigma D_{bN} W_N \qquad (23)$$

[wherein $W_N$ is a factor to convert each (i,j,k) region to its ratio to the real volume of an irradiated field so as to be multiplied with the absolute value of $D_b$]. If each region (i,j,k) has an equal area, the following formula is introduced;

$$D_b = W_N \Sigma D_{bN} \qquad (24)$$

By doing like this, the three-dimensional calculation can be executed for a time period several fold the time needed for two-dimensional calculation. Alternatively, when i, j and k are from 1 to 40, the conventional method would require the calculating time forty fold the time necessary for two-dimensional calculation. In the conventional radiotherapy treatment planning system employing the conventional ETAR method, accurate introduction of the three-dimensional contribution into two-dimensional contribution, on the basis of such distribution of contribution, has not been taken into account, so a large error has sometimes appeared.

By using various sizes of (i,j,k) depending on the slope of a distribution of contribution, the size of the region (i,j,k) can be made larger at a point with a more gradual slope. Thus, the deterioration of the precision can be prevented while shortening computing time. In the formula, (23), for example, the slope of the distribution of contribution to the point B is rather small in the slices 52 and 54 except the slice 53 including the point B. Calculation is carried out using a wider size as follows;

$$D_b = {}_N\Sigma D_{bN} W_N \qquad (25)$$

($W_{53} < W_{52} = W_{54}$) [wherein the ratio of $W_{53}$ to $W_{52}$ should be employed so that the volumetric ratio can be corrected]. In other words, in the subject-region determining unit 25, the size should be made larger, corresponding to the unit with a more gradual slope of the distribution of contribution. Other than that, even within the identical slice, the size may be modified corresponding to the slope of the distribution of contribution. Alternatively, the electron density between the slices may be applied to the size determined by interpolation.

There may be also used the values of TPR and SPR, corresponding to the dose within the subject region. The equivalent depth $d_n$ can be determined by the formula; $\tilde{d} = {}_i\Sigma d_i \rho_i$, wherein d is the depth; s is the area of an irradiated field; and r is the equivalent radius (r=2A/P; P is circumference length of area of an irradiated field.). The corrected radius $r_n$ is determined by the formula:

$$r_n = \rho_n r$$

$\rho_n$ is represented by the formula;

$$\rho_n = \frac{\Sigma_j \Sigma_k \Sigma \rho(i, j, k) \eta_b(i, j, k)}{\Sigma_j \Sigma_k \Sigma \eta_b(i, j, k)} \quad (26)$$

That is, $D_c = d \cdot TPR(d_n, r_n)$, (d is a constant). $D_c$ is the dose at the isocenter.

If such a manner is performed, the variation of TPR values in irradiation systems, due to the difference of manufactures, can be suppressed without correcting $\eta_b(i,j,k)$. By comparing $\eta_n$ and $d_n$ with $\rho$ and d, respectively, the error in such calculation can be also checked. Instead of TPR values, TAR and PDD values may be also used. TPR value is tissue-phantom ratio, while TAR value is tissue-air dose ratio, PDD value being a percentage in dose depth.

Only the dose from a region with a high contribution rate may be determined by the formula (21) and (23), and then the dose from a region with a low contribution rate may be determined by the value of SPR. That is, $$D_b = \Sigma_j \Sigma_k \Sigma \rho(i, j, k) \eta_{eb}(i, j, k) + a \int_0^{2\pi} \frac{SPR[d, r(\theta)]}{2\pi} d\theta \quad (27)$$

In the formula (27), a first term on right side is due to direct beam and a second term is in relation with scattered beam, "a" being a factor including field factor. SPR means herein scattering-peak/dose ratio.

In the calculation at the arithmetic unit 26, calculation by addition is done mainly, so the calculation under fixed point can be carried out, resulting in calculation with high speed in case that an electronic computer is used as a radiotherapy treatment planning system. Because exponential calculation and division are so often carried out in the conventional ETAR method and the like, calculation under floating point is required, resulting in a longer computing time.

As the radiotherapy treatment planning system is thus constructed such that a region with a higher contribution rate is employed as arithmetic subject and the arithmetic matrix size is changeable, there is obtained the effect of outputting dose with a high speed, without reducing arithmetic precision so much.

As the contribution ratio to the observational point is calculated in this invention, varying of matrix size is possible. On the other hand, convolution method uses the contribution ratios of scattering points, so the matrix size is not able to be changeable in case of using the method.

FIG. 19 is a block diagram to show a real-time arithmetic result display system suitable for a radiotherapy treatment planning system according to an embodiment of the present invention. In FIG. 19, the FIG. 101 represents a displacement input unit, which comprises a truck ball or a rotary switch, provided with a potentiometer required for transformation of the input to the system from an operator, into an electric signal corresponding to the input. 102A is a main arithmetic unit, comprising a digital computer of a required scale. 103 is a high-speed arithmetic unit comprising an array processor or the like, to perform the required calculation of dose distribution with a high speed. 104 is an image memory, to memorize the arithmetic results of dose distribution by the high-speed arithmetic unit 103, in order to display the results on desirable images. 105 is a character-display CRT and 106 is a key board, both of which perform the necessary functions as man-machine interface between an operator and the system. 107 is a graphic CRT, to display on its scope the contents stored in the image memory 104.

FIG. 20 is a flow chart to explain the operation of the system. FIG. 20(A) is a flow chart to explain an interrupt operation; FIG. 20(B) is a flow chart to explain a preset task operation.

Next, operation of the above system will be explained now with reference to FIGS. 19 and 20.

The above system is now assumed to be in continuous routine operation. The system described above is then in high-precision arithmetic and display operation, which is set so that interrupt operation may start at a constant cycle with a suitable inner timer (not shown in the figure). The interrupt operation will now be explained, mainly with reference to FIG. 20(A). Firstly at step S21, interruption will start with a suitable timer described above. At next step S22, a preset displacement is input through the displacement input unit 101. At the subsequent step S23, judgment is done whether or not there is a change in the input displacement. When the result of such judgment is NO, interrupt operation is terminated, after skipping to step S29. In other words, routine arithmetic and display operation with high precision is then made to continue.

On the other hand, when the result of such judgment at step S23 is YES, the continuation of routine arithmetic and display operation with high precision is then made to stop by transferring to step S24. In other words, the execution of the task for arithmetic and display operation with high precision is terminated. At its subsequent step S25, the input displacement is transformed into its corresponding arithmetic parameters which are then input and stored in a suitable memory means (not shown in figures) in order to use them for the subsequent arithmetic and display operation with high precision. At next step S26, the calculation by a preset simple formula by means of a high-speed arithmetic unit 103 is executed. At the subsequent step S27, the results of the previous calculation are written into an image memory 104. Such write is realized by overwriting on the data having already been written. Additionally, at the step S27, a new image is displayed on a graphic CRT 107. At the following step S28, the task for arithmetic and display operation with high precision is reinitialized.

The execution of the task will now be explained, mainly with reference to FIG. 20(B). Following task start at step T21, read out of the parameters in storage is executed (T22), and calculation with high precision is then executed by using the parameters (T23). The arithmetic results are displayed by using the image memory 104 and the graphic CRT 107.

As the calculation with high precision herein described requires a long processing time, the execution of the calculation with high precision is interrupted in terms of the operation from step S24 to step S28 in FIG. 20(A), when there is observed a change in the displacement input from the displacement input unit 101 during the calculation and display. After an appropriate time has passed, the calculation with high precision, based on the modified displacement, is resumed.

In the above embodiments, a truck ball or rotary switch may be used as a displacement input unit; mouse, digitizer, and joystick may be also used, instead of it.

Although graphic CRT is illustrated as a display system, it is not limited to. An appropriate and desirable device such as LCD, EL, plasma display and the like may be used as well.

In the above embodiments, a radiotherapy treatment planning system is illustrated, but similar effects and actions can be obtained in some means where the arithmetic results can be displayed on real time in appropriate embodiments such as numerical figures, graphs, images and the like, the means being illustrated as various measuring devices, control boards, CAD, CG, medical image display systems and the like.

A variety of the control function units of the present invention for the detection of the change in input displacement and the like, for example, can be realized in a hardware structure composed of appropriate electric circuits.

Furthermore, the contents of the calculation according to the process of the present invention can take into account real-time image processing including real-time zoom, rotation, slice reconstitution and the like, and spectrum display on various measuring devices.

As has been described above, the real-time arithmetic result display system in accordance with the present invention, is provided with a displacement input unit, a first arithmetic unit for executing the calculation based on a preset high-precision formula when no change is observed in the displacement, a second arithmetic unit for executing the calculation based on a preset simple formula when any change is observed in the displacement, and a display system for displaying the arithmetic results by the first or second arithmetic unit, which is characterized in that the calculation with a high precision is constantly performed by the first arithmetic unit and the calculation using the high-precision formula by the first arithmetic unit is interrupted when change is observed in the displacement, to execute the calculation using a simple formula by the second arithmetic unit, whereby there can be obtained the effects such that only simple switching of arithmetic condition in a hardware structure similar to conventional ones can economically realize a radiotherapy treatment planning system with high precision.

What is claimed is:

1. Radiotherapy treatment planning apparatus for calculating the absorbed dose of radiation irradiated by a radiation source at an observational point within an object to be irradiated, on the basis of the absorbed dose due to the radiation scattered at points other than said observational point and the absorbed dose due to the electron beam generated by the radiation incident to said other points, said radiotherapy treatment planning apparatus comprising:

radiation source apparatus for directing radiation to said observational point whereby electron beams are generated by the radiation incident at said observational point and at said points other than said observational point;

a distribution of contribution output unit for outputting a distribution of contribution representing the distribution, in the object to be irradiated, of the contribution rates of said radiation to said observational point, and an arithmetic unit having means for determining the absorbed dose due to the radiation scattered at the observational point by multiplying the output contribution rates from the distribution of contribution output unit with the electron densities at individual points corresponding to these contribution rates and by summing up the multiplied contribution rates.

2. The radiotherapy treatment planning apparatus as defined in claim 1, wherein said distribution of contribution output unit includes means for calculating the contribution rates by using the electron density corrected length which is obtained by correcting the depth of the observational point in the object to be irradiated with the electron density $\rho$ in the region from the observational point to the radiation source.

3. The radiotherapy treatment planning apparatus as defined in claim 2, wherein said distribution of contribution output unit includes means for calculating on a simplified basis the contribution rates by defining $\cos \theta_i = 1$ when the angle $\theta_i$ is small, the angle being made by the straight line from the observational point leading to the radiation source and the straight line from the observational point leading to the scattered point.

4. The radiotherapy treatment planning apparatus as defined in claim 2, wherein said distribution of contribution output unit includes means for calculating the contribution rates to take into account the heterogeneity of the electron density of the object to be irradiated in the direction orthogonal to the direction from the observational point leading to the radiation source.

5. The radiotherapy treatment planning apparatus as defined in claim 2, wherein said distribution of contribution output unit includes means for calculating the contribution rates by using the approximation $e^{-x} = 1 - x$.

6. Radiotherapy treatment planning apparatus for calculating the absorbed dose of radiation irradiated by a radiation source at an observational point within an object to be irradiated, on the basis of the absorbed dose due to the radiation scattered at points other than said observational point and the absorbed dose due to the electron beam generated by the radiation incident to the other points, said radiotherapy treatment planning apparatus, comprising:

radiation source apparatus for directing radiation to said observational point whereby electron beams are generated by the radiation incident at said observational point and at said points other than said observational point;

a distribution of contribution output unit for outputting a distribution of contribution representing the distribution, in the object to be irradiated, of the contribution rates of said electron beam to said observational point, a subject setting unit including means for defining a subject region where said other points are present provided that said observational point is present within a range of the electron beam from said other points, and an arithmetic unit having means for determining the absorbed dose due to the radiation scattered at the observational point by multiplying the output contribution rates from the distribution of contribution output unit with the electron density at the individual points within the region determined by the subject setting unit and by summing up the multiplied contribution rates.

7. The radiotherapy treatment planning apparatus as defined in claim 6, wherein such distribution of contribution output unit includes means for calculating the contribution rates by using the electron density corrected length which is obtained by correcting the depth of the observational point in the object to be irradiated with the electron density $\rho$ in the region from the observational point to the radiation source.

8. The radiotherapy treatment planning apparatus as defined in claim 7, wherein said subject setting units includes means for determining the subject region by summing up the electron densities in the individual micro-regions in the object to be irradiated in the direction from the observational point leading to the radiation source and by defining the region where the sum reaches a range of electron beam's reach.

9. The radiotherapy treatment planning apparatus as defined in claim 7, wherein said subject setting unit includes means for determining the subject region by summing up the electron densities in the individual micro-regions in the object to be irradiated in the direction from the observational point leading to the radiation source and also in the direction orthogonal to the direction from the observational point leading to the radiation source, at a preset sequence, and by defining the region where the sum reaches a range of electron beam's reach.

10. The radiotherapy treatment planning apparatus as defined in claim 7, wherein said distribution of contribution output unit includes means for calculating the contribution rates by correcting the distance from the observational point to the scattering point with the mean value of the electron densities $\rho_a$ and $\rho_b$, corresponding to the two points, respectively, and using the corrected value of the distance.

11. Radiotherapy treatment planning apparatus for calculating the absorbed dose of radiation irradiated by a radiation source at an elevational point within an object to be irradiated, on the basis of the absorbed dose due to the radiation scattered at points other than said observational point and the absorbed dose due to the electron beam generated by the radiation incident to the other points said radiotherapy treatment planning apparatus comprising:

radiation source apparatus for directing radiation to said observational point whereby electron beams are generated by the radiation incident at said observational point and at said points other than said observational point;

a data unit for outputting a distribution of contribution representing the distribution, in the object to be irradiated, of the contribution rates of said scattered radiation to said observational point, a subject region determining unit including means for determining the region, in the object to be irradiated, having a preset contribution rate or a higher contribution rate among said contribution distribution, and for determining the arithmetic matrix size concerning the region, and an arithmetic unit including means for determining the absorbed dose of the observational point due to the scattered radiation by multiplying the contribution rates of the scattered radiation at the individual points in the region determined by the subject region determining unit with the electron densities at said individual points and by summing up the multiplied contribution rates.

12. The radiotherapy treatment planning apparatus as defined in claim 11, wherein said subject region determining unit includes means for determining a region with a higher contribution on the basis of the density of a CT image of the object to be irradiated.

13. The radiotherapy treatment planning apparatus as defined in claim 12, wherein said arithmetic unit includes means for calculating the absorbed dose by adding the contribution of the region on other CT slices to the CT slice where the observational point is present.

14. The radiotherapy treatment planning apparatus as defined in claim 11, wherein said subject region determining unit includes means for making larger the size of the arithmetic subject region at the part with a small slope of the contribution distribution.

15. Radiotherapy treatment planning apparatus including means for calculating the absorbed dose of radiation irradiated by a radiation source at an observational point within an object to be irradiated, on the basis of the absorbed dose due to the radiation scattered at points other than said observational point and the absorbed dose due to the electron beam generated by the radiation incident to the other points, said radiotherapy treatment planning apparatus comprising:

radiation source apparatus for directing radiation to said observational point whereby electron beams are generated by the radiation incident at said observational point and at said points other than said observational point;

a data unit for outputting a distribution of contribution representing the distribution, in the object to be irradiated, of the contribution rates of said generated electron beam to said observational point, a subject region determining unit including means for determining the region, in the object to be irradiated, having a preset contribution rate or a higher contribution rate among said contribution distribution, and for determining the arithmetic matrix size concerning the region, and an arithmetic unit including means for determining the absorbed dose of the observational point due to the generated electron beam by multiplying the contribution rates of the generated electron beam at the individual points in the region determined by the subject determining unit with the electron densities at said individual points and by summing up the multiplied contribution rates.

16. The radiotherapy treatment planning apparatus as defined in claim 15, wherein said subject region determining unit includes means for determining a region with a higher contribution on the basis of the density of a CT image of the object to be irradiated.

17. The radiotherapy treatment planning as defined in claim 16, wherein said arithmetic unit includes means for calculating the absorbed dose by adding the contribution of the region on other CT slices to the CT slice where the observational point is present.

18. The radiotherapy treatment planning apparatus as defined in claim 15, wherein said subject region determining unit includes means for making larger the size of the arithmetic subject region at the part with a small slope of the contribution distribution.

* * * * *

UNITED STATES PATENT AND TRADEMARK OFFICE
CERTIFICATE OF CORRECTION

PATENT NO. : 5,291,404
DATED : March 1, 1994
INVENTOR(S) : Masaaki Kurokawa et al.

It is certified that error appears in the above-indentified patent and that said Letters Patent is hereby corrected as shown below:

Col. 7, line 3, after "formula" insert -- (1) -- Col. 8, line 57, "$D_{sb}={}_i\Sigma_j\Sigma_k\Sigma\rho(i,j,k)\rho_{xb}(i,j,k)$" should be -- $D_{sb}={}_i\Sigma_j\Sigma_k\Sigma\rho(i,j,k)\eta_{xb}(i,j,k)$ --; Col. 9, line 47, "exp}" in the formula should be -- exp{ --; Col. 9, line 52, after "point B)" insert -- is small. --; Col. 11, line 8, the formula "$D_{eb}={}_i\rho_j\Sigma_k\rho\rho(i,j,k)\rho_{eb}(i,j,k)$" should be -- $D_{eb}={}_i\Sigma_j\Sigma_k\Sigma\rho(i,j,k)\eta_{eb}(i,j,k)$ --; Col. 12, line 30, the formula "$\rho_T={}_i\rho_j\Sigma_k\Sigma\rho(i,j,k)W_b(i,j,k)$" should be -- $\rho_T={}_i\Sigma_j\Sigma_k\Sigma\rho(i,j,k)W_b(i,j,k)$ --; Col. 13, line 47, the formula "$D_b={}_i\Sigma_j\Sigma_k\Sigma\rho(i,j,k)\rho_b(i,j,k)$" should be -- $D_b={}_i\Sigma_j\Sigma_k\Sigma\rho(i,j,k)\eta_b(i,j,k)$ --; Col. 14, line 1, "18(B)j" should be -- 18(B)]. --; Col. 15, line 10, "$\eta_n$" should be -- $\rho_n$ --; Col. 15, line 17, "formula" should be -- formulas --.

Signed and Sealed this

Twelfth Day of July, 1994

Attest:

BRUCE LEHMAN

Attesting Officer

Commissioner of Patents and Trademarks